United States Patent
Manusu et al.

(12) 
(10) Patent No.: US 6,413,402 B1
(45) Date of Patent: Jul. 2, 2002

(54) CASSETTE FOR ELECTROPHORETIC GELS

(75) Inventors: Howard Pericles Manusu, Hunters Hill; Shaun Atchison, North Ryde, both of (AU)

(73) Assignee: Gradipore Limited, Frenchs Forest NSW (AU)

( * ) Notice: Subject to any disclaimer, the term of this patent is extended or adjusted under 35 U.S.C. 154(b) by 0 days.

(21) Appl. No.: 09/543,855

(22) Filed: Apr. 5, 2000

(30) Foreign Application Priority Data

Apr. 6, 1999 (AU) .............................................. PP9606

(51) Int. Cl.[7] .......................... G01N 27/26; B29C 33/00
(52) U.S. Cl. ........................ 204/620; 204/619; 204/618; 249/117
(58) Field of Search ....................... 204/616, 618–620; 249/117

(56) References Cited

U.S. PATENT DOCUMENTS 5,543,023 A * 8/1996 Logojan ..................... 204/618
5,954,934 A * 9/1999 Manusu ...................... 204/618

* cited by examiner

*Primary Examiner*—T. Tung
*Assistant Examiner*—Alex Noguerola
(74) *Attorney, Agent, or Firm*—Baker & McKenzie

(57) ABSTRACT

An improved cassette for use in the formation of an electrophoretic gel comprises two plates with substantially planar walls having two sides and two ends so arranged in a side by side spaced apart array to form a gel receiving space between them. A plurality of dividing ribs on one or each of the walls extend from a first end of the wall or walls substantially parallel to at least one of the sides thereof to a rib base end. The ribs extend into the space so as to subdivide at least one end of the space into a plurality of substantially parallel wells. A plurality of holes extend through at least one of the walls of the cassette located at or adjacent the base of the dividing rib and aligned with the rib. The arrangement of holes allow sufficient current flow to replace that lost due to the dividing ribs. The structure retains the advantage of having solid dividing walls which are considerably more resilient than dividing walls made from fingers of gel even when reinforced with pegs or projections, and yet by virtue of the provision of a hole at the base of the ribs allows sufficient current flow at the base of each rib that the current flow through the space is substantially uniform, thus preventing spreading of the bands as they form in the body of the gel.

7 Claims, 2 Drawing Sheets

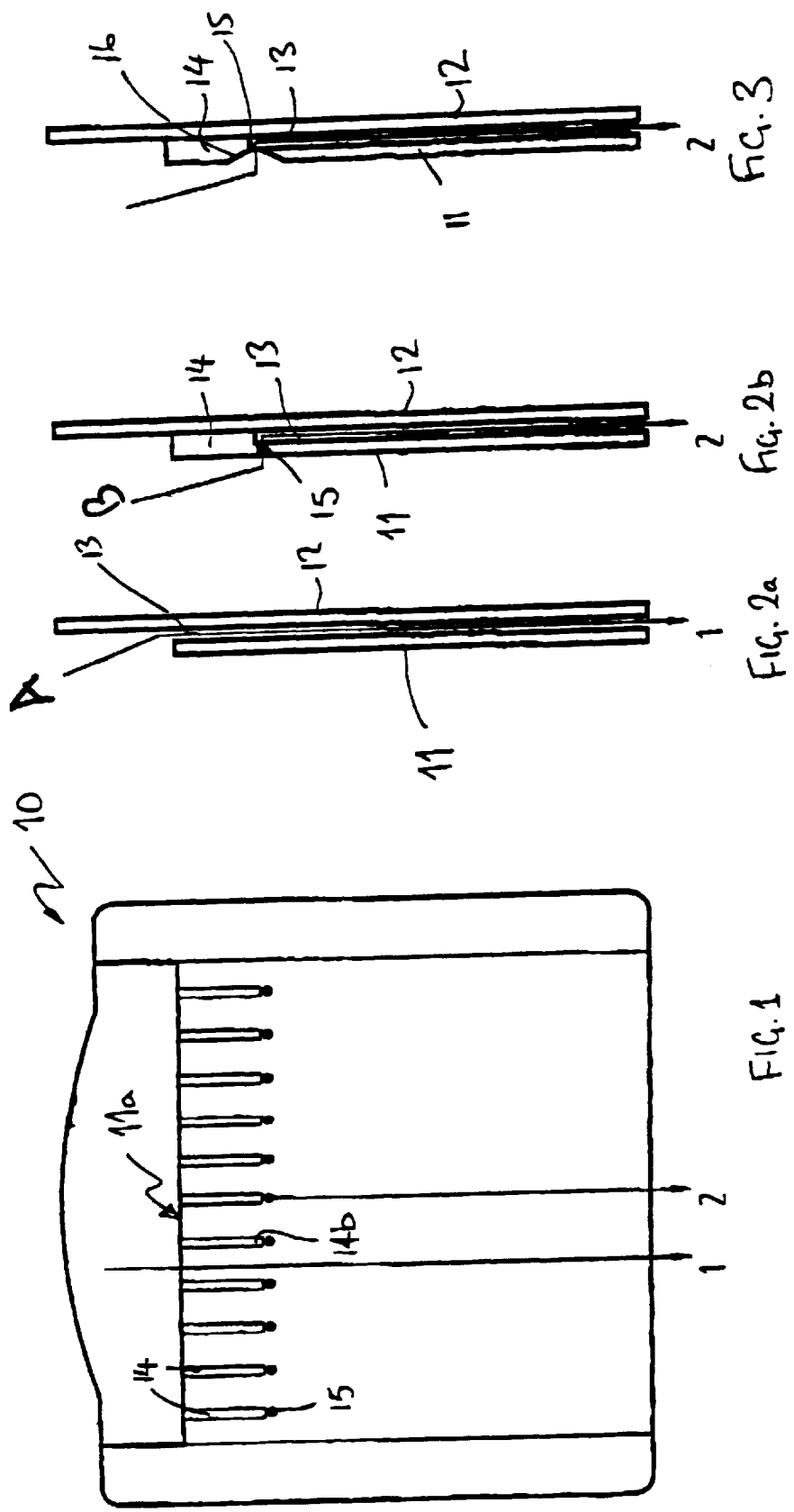

CASSETTE FOR ELECTROPHORETIC GELS

FIELD OF THE INVENTION

The present invention relates to a cassette for use in the formation of an electrophoretic gel and more particularly to such a cassette which includes means to assist in separating and defining individual sample receiving wells at one end of the electrophoretic gel.

BACKGROUND ART

Electrophoretic gels, usually comprising hydrogels such as agarose or polyacrylamide are used for the separation of nucleic acids, proteins and other macromolecular compounds. The sample to be separated is placed at one end of the gel and a direct electric field is applied between the ends of the gel causing the components of the sample to migrate through the gel at rates dependent upon their molecular size and charge.

A mixture of components to be separated is normally introduced into one of a number of small wells formed in an upper edge of the gel before the electric current is applied. It is usual to run a number of such mixtures simultaneously on an electrophoretic gel in a side by side arrangement. For this purpose one mixture is placed in each of a series of wells formed in the upper edge of the gel.

In the past electrophoretic gels were formed by juxtaposing a pair of glass plates in a slightly spaced apart side-by-side relationship and filling the space therebetween with a liquid which can set and form an electrophoretic gel. The side edges of the space between the glass plates were typically sealed with adhesive tape or a similar material, and when the gel is poured a comb was placed in the upper end of the space between the glass plates. After the gel had set the comb would be withdrawn leaving a series of spaced apart wells defined in the top of the gel each well having been defined by one tooth of the comb. A tongue of gel remains between the glass plates separating the pair of adjacent wells.

The gel is immersed in a buffer solution and electrodes above and below the gel cause a direct electric current to flow through the gel. The components in the mixtures travel through the gel from the top to the bottom of the gel at different rates depending on their size and charge, and separate out into bands.

In more recent years it has been proposed to preform electrophoretic gels in cassettes formed of synthetic plastics materials. The side walls of the cassette are formed with integral means to connect them together along the sides of the cassette. Again when the gel is poured a comb is placed in the upper end of the space between the walls of the cassette for the formation of the spaced apart wells. However, this arrangement has a disadvantage that upon withdrawal of the comb the fingers of the gel may, with time, show an increased tendency to break away from the remainder of the gel. This results in poorly defined wells. Alternatively, if the tongues of gels are left intact upon withdrawal of the comb they may not firmly adhere to the plastic side wall of the cassette. This has resulted that the tongues may fall over side ways occluding an adjacent well.

One attempt to overcome this problem is described in U.S. Pat. No. 5,288,465, where ribs are provided in the cassette walls to define wells at one end of the cassette. Whilst this arrangement provides stable wells suitable to hold the sample material, this arrangement has a disadvantage that the solid walls of the wells interfere with the smooth flow of electric current through the electrophoretic gel: because of the ribs, the current is initially confined and then spreads out which has a result that as the run proceeds bands from adjoining wells tend to spread out and merge with one another.

International Patent Application No WO 97/04307 addresses the problem of current interference by replacing the ribs by a plurality of small projections or pegs. These projections or pegs extend into the gel to support the gel fingers. The projections support the gel whilst allowing substantially parallel flow of the current to establish before the current meets the samples positioned in the bottom of the wells. This parallel current flow is necessary to maintain the separation between the bands/samples from the different wells and prevent the samples for spreading outwards.

However, the disadvantage of the cassette shown in WO 97/04307 is that as the combs are withdrawn, the tops of the gel fingers tend to break away from the remainder of the gel finger.

The present invention is directed to alternative arrangements addressing the problems associated with spreading current and also the integrity of the walls of the sample wells.

DISCLOSURE OF THE INVENTION

According to a first aspect of the present invention there is provided an improved cassette for use in the formation of an electrophoretic gel comprising two plates with substantially planar walls having two sides and two ends so arranged in a side by side spaced apart array to form a gel receiving space between them, a plurality of dividing ribs on one or each of the walls extending from a first end of the wall or walls substantially parallel to at least one of the sides thereof to a rib base end and being adapted to extend into the space so as to subdivide at least one end of the space into a plurality of substantially parallel wells, the improvement consisting of a plurality of holes extending through at least one of the walls of the cassette located at or adjacent the base of the dividing rib and aligned with the rib, the arrangement being such that the holes allow sufficient current flow to replace that lost due to the dividing ribs.

The present invention retains the advantage of having solid dividing walls which are considerably more resilient than dividing walls made from fingers of gel even when reinforced with pegs or projections, and yet by virtue of the provision of a hole at the base of the ribs allows sufficient current flow at the base of each rib that the current flow through the space is substantially uniform, thus preventing spreading of the bands as they form in the body of the gel.

The size of the gap between the sample bands can be controlled by varying the size of the hole in the wall of the cassette. A larger hole creates a greater current flow and provides a wider gap between the samples. The size of the hole will depend on the thickness of the rib and the size of the well. The holes may vary in size between about 2 mm diameter to 0.5 mm diameter, with a 1 mm diameter hole being typical.

It is a preferred feature that the ribs are tapered outwardly from the first end to their base end so that the upper part of the well is wider than the lower part of the well. This makes the wells easier to load with samples.

It is preferred that the sides of the holes are chamfered or tapered so that during operation the chamfered hole will fill with buffer and not trap air bubbles.

In gel cassettes of the type described above and in the introduction, the concentration of the gels is graduated. The cassettes are typically filled from below which means that the gel at the top of the cassette which is the least dense, is the least concentrated. Ironically, in cassettes of the type where gel fingers form, the walls of the well is also the part where the gel needs to be strongest i.e. the most concentrated gel. Thus, there is a requirement for the concentration of acrylamide in such cassettes to be high to ensure a high enough gel concentration for forming the fingers. However, in the present invention because the walls of the well are plastic and not gel, the upper zone of the gel can be a much lower concentration say around 2.5% as opposed to 5% which allows the separation of a much higher molecular weight proteins having a molecular weight of around 800,000 to 1,000,000.

A second aspect of the present invention provides an improved cassette containing an electrophoretic gel comprising two plates with substantially planar walls having two sides and two ends so arranged in a side by side spaced apart array to form a gel receiving space between them, a plurality of dividing ribs on one or each of the wall members extending from the first end of the member or members substantially parallel to at least one of the sides thereof and adapted to extend into the space so as to subdivide at least one end of the space into a plurality of substantially parallel wells having bases, the improvement comprising that the part of the well walls formed from plastic rib material does not extend to the base of the well and that the lower part of the well wall is formed from a finger of gel.

In one preferred embodiment, the finger of gel may be supported by one or more projections.

The solid upper rib segment of the well wall resists stresses placed on the gel fingers and maintains the integrity of the wells. It prevents damage to the lower gel fingers defining the lower part of the well walls when the comb is withdrawn or when samples are loaded into the wells. Surprisingly the gel base of the wall allows the re-establishment of parallel current flow through the gel before the well base is reached by the current maintaining the separation between the bands of separating molecules in the body of the gel.

BRIEF DESCRIPTION OF THE DRAWINGS

The invention will now be described, by way of example only, and with reference to the accompanying drawings in which:

FIG. 1 is a schematic front view of a cassette illustrating a first embodiment of the present invention;

FIGS. 2a and 2b are schematic side views illustrating current flow through the cassette shown in FIG. 1;

FIG. 3 is a side view of a variant of the embodiment shown in FIG. 1;

BRIEF DETAILED DESCRIPTION OF THE PREFERRED EMBODIMENTS

Figure 5:
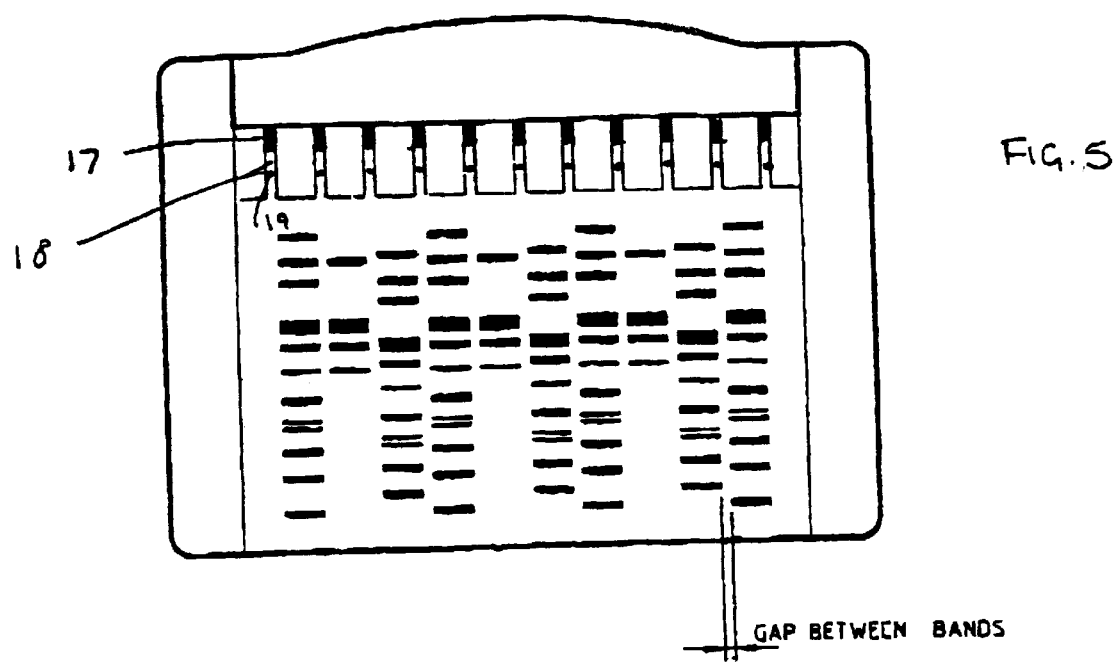
FIG. 5 shows a second embodiment of the present invention also illustrating separation between bands of molecules separated by electrophoresis.

Referring to the drawings FIG. 1 shows a first electrophoresis cassette 10 which may be formed in two parts by injection moulding or by other methods from a suitable synthetic plastic material.

One part forms a first side wall 11 of the cassette which is banded on each side by a connecting means comprising a pair of spaced apart ridges not shown.

The other part forms a second side wall 12 of the cassette which is also banded on each side by a pair of spaced ridges, not shown. The ridges interdigitate to form a seal along each side of the cassette to prevent leakage therethrough of the gel forming liquid during setting of the gel or flow of an electrical current during electrophoresis.

The ridges are of a sufficient thickness that a gel receiving space 13 is defined between the side walls which lie in substantially parallel planes. Such a construction as described above is already well known in the prior art see, for example. WO 97/04307 the contents of which are incorporated herein by reference.

The inside surface of the side wall 11 is formed with a plurality of inwardly directed parallel, spaced apart ribs 14 which extend into the gel receiving space 13.

The ribs 14 may however originate from either or both of walls 11 and 12. Each rib has a length which defines the depth of the well, and a thickness which spans the gel receiving space 13.

The ribs 14 extend from a first, upper end 11a of side wall 11 to a base end 14b which is located at the base of the well.

In an alternative embodiment, the ribs may be thicker than the gel receiving space 13 and they may mate with corresponding recesses provided in the opposite wall 12.

At the base of each rib distal from the upper end 11a of the side wall 11 there is a hole 15 which extends through the wall 11 and is typically around 1 mm diameter.

To form a gel in the cassette 10 a comb with a plurality of spaced apart teeth is inserted into the upper end of the cassette. The teeth are dimensioned so that they interdigitate with the ribs 14 but are at all times closely spaced therefrom. After the gel is formed in the space 13 the cassette can be used.

When the comb is withdrawn, there will be a plurality of wells formed in the gel separated by the ribs 14.

In use the cassette is inserted in a buffer solution and current is passed through the gel via an electrode located above the upper end of the cassette and an electrode located below the lower of end of the cassette. Current flows in two paths, the first path being through the well illustrated by arrow (A) shown in FIG. 2a and the second path (B) through the hole 15 thence through the gel to the base of the cassette.

It is that additional flow of current through the hole 15 that prevents the current passing through the wells from spreading out and intermingling the bands.

The separation of the samples into bands of molecules is illustrated in FIG. 5, albeit in the context of a definite embodiment of the invention. The gap between bands can be varied by varying the size of the hole 15.

FIG. 3 shows a variant in which the side 16 of the hole 15 are tapered outwardly or chamfered to allow buffer to fill the hole more easily and to prevent air bubbles becoming trapped in the hole 15. An air bubble would inhibit the passage of electric current through the hole defeating the object of the invention.

Figure 4:
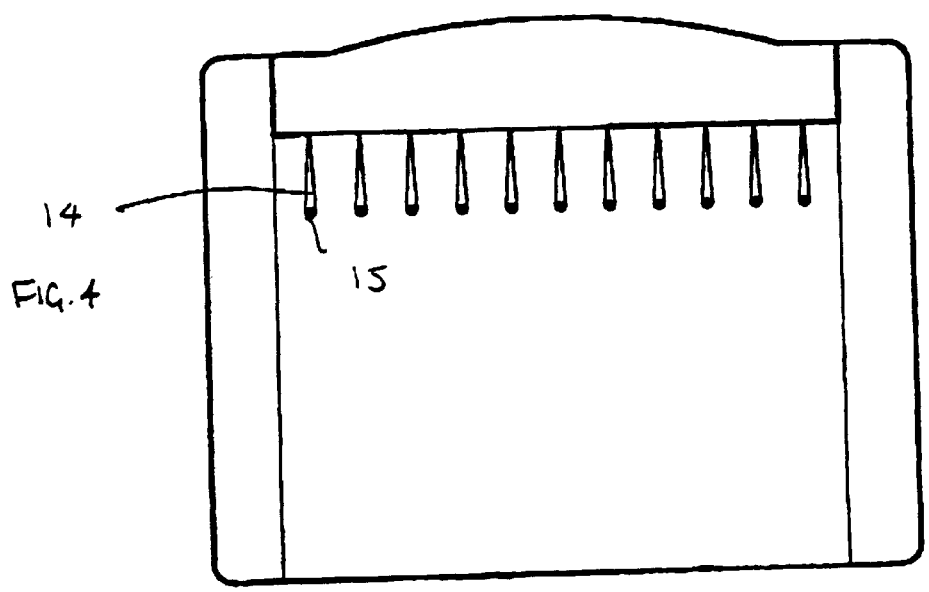
FIG. 4 shows a further variant of the embodiment shown in FIG. 1.

FIG. 4 shows a further variant on the invention in which the ribs 14 are tapered being wider at their base portion adjacent the hole 15 and narrower at the top portion adjacent the upper edge of side wall 11. This makes the upper part of the wells wider and makes loading the wells easier.

FIG. 5 shows a further embodiment of the present invention in which the upper part of the walls of the dividing well are comprised of plastic ribs 17 and the lower part of the walls comprise a gel finger 18 which may be stabilised with one or more pegs 19 such as described in WO 97/04307.

The solid upper part of the rib resists stresses placed on the fingers and maintains integrity of the walls, particularly when the comb is being withdrawn or when samples are being loaded into the wells. Because the lower part of the well walls comprises a gel finger, this allows the current to spread out sufficiently before it reaches the samples, for separation to occur in even bands as illustrated in FIG. 4.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A cassette for use in the formation of an electrophoretic gel comprising two plates with substantially planar walls having two sides and two ends so arranged in a side by side spaced apart array to form a gel receiving space between them, a plurality of dividing ribs on one or each of the walls extending from a first end of the wall or walls substantially parallel to at least one of the sides thereof to a rib base end and being adapted to extend into the space so as to subdivide at least one end of the space into a plurality of substantially parallel wells, the improvement consisting of a plurality of holes extending through at least one of the walls of the cassette located at or adjacent the base of the dividing rib and aligned with the rib, the arrangement being such that the holes allow additional current flow to replace that lost due to the dividing ribs.

2. The cassette of claim 1 wherein the plurality of holes may vary in size between about 2 mm diameter to 0.5 mm diameter.

3. The cassette of claim 1 or claim 2 wherein the holes have a diameter of about 1 mm.

4. The cassette of claim 1 wherein the ribs are tapered outwardly from an upper end to their base end so that the upper part of the well is wider than the lower part of the well.

5. The cassette of claim 1 wherein the sides of the holes are chamfered or tapered.

6. An improved cassette containing an electrophoretic gel comprising two plates with substantially planar walls having two sides and two ends so arranged in a side by side spaced apart array to form a gel receiving space between them, a plurality of dividing ribs on one or each of the wall members extending from the first end of the member or members substantially parallel to at least one of the sides thereof and adapted to extend into the space so as to subdivide at least one end of the space into a plurality of substantially parallel wells having bases, the improvement comprising that the part of the well walls formed from plastic rib material does not extend to the base of the well and that the lower part of the well wall is formed from a finger of gel.

7. The cassette of claim 6 wherein the finger of gel is supported by a one or more projections.

* * * * *